United States Patent

Schmidt-Kaeding

(10) Patent No.: US 9,915,605 B2
(45) Date of Patent: Mar. 13, 2018

(54) IN-SITU GAS-MEASURING SYSTEM FOR GAS REACTORS WITH CRITICAL ENVIRONMENTS

(71) Applicant: Dräger Safety AG & Co. KGaA, Luebeck (DE)

(72) Inventor: Patrick Schmidt-Kaeding, Luebeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 15/462,021

(22) Filed: Mar. 17, 2017

(65) Prior Publication Data

US 2017/0268992 A1 Sep. 21, 2017

(30) Foreign Application Priority Data

Mar. 18, 2016 (DE) .................... 10 2016 003 285

(51) Int. Cl.
*G01N 21/3504* (2014.01)
*G01N 21/09* (2006.01)
*G01N 21/03* (2006.01)

(52) U.S. Cl.
CPC ......... *G01N 21/3504* (2013.01); *G01N 21/09* (2013.01); *G01N 2021/0314* (2013.01); *G01N 2021/3513* (2013.01); *G01N 2201/024* (2013.01); *G01N 2201/0227* (2013.01); *G01N 2201/086* (2013.01)

(58) Field of Classification Search
CPC ................... G01N 21/3504; G01N 21/3513
USPC ..................................... 250/339.13
See application file for complete search history.

(56) References Cited

U.S. PATENT DOCUMENTS

| 6,903,823 B1* | 6/2005 | Muller ............... G01N 21/03 356/437 |
| 9,234,905 B2 | 1/2016 | Ido et al. |
| 2009/0022205 A1* | 1/2009 | Comendant .......... G01K 1/16 374/161 |

FOREIGN PATENT DOCUMENTS

| CN | 102 062 726 A | 5/2011 |
| DE | 199 44 260 A1 | 4/2001 |

* cited by examiner

*Primary Examiner* — David Porta
*Assistant Examiner* — Meenakshi Sahu
(74) *Attorney, Agent, or Firm* — McGlew and Tuttle, P.C.

(57) ABSTRACT

An in-situ gas-measuring system (1) includes an IR photon source (10) and an IR photon detector (11). The in-situ gas-measuring system (1) has an expansion chamber (12), at which an optical element (16, 16', 16") is arranged. A connection element (13) provides a detachable fluid-communicating connection of the expansion chamber (12) to a gas reaction chamber (2). The IR-photon source (10), the optical element (16, 16', 16") and the IR photon detector (11) define an optical measuring path, which extends through the expansion chamber (12). The installation and maintenance of the in-situ gas-measuring system (1) are reduced by the features of the in-situ gas-measuring system (1).

13 Claims, 3 Drawing Sheets

IN-SITU GAS-MEASURING SYSTEM FOR GAS REACTORS WITH CRITICAL ENVIRONMENTS

CROSS REFERENCE TO RELATED APPLICATIONS

This application claims the benefit of priority under 35 U.S.C. § 119 of German Application 10 2016 003 285.5 filed Mar. 18, 2016, the entire contents of which are incorporated herein by reference.

FIELD OF THE INVENTION

The present invention pertains to an in-situ gas-measuring system comprising a gas-measuring device with an infrared photon source (IR photon source) and an IR photon detector (IR photon detector).

BACKGROUND OF THE INVENTION

In gas reactors or enclosed environments, in which critical gas concentrations may be present, gas measurements are necessary in order to detect gases being released or too high concentrations of toxic or explosive gases. The environment-related variables in the gas reactors or in the enclosed environments are frequently critical, i.e., very cold, very hot and/or highly reactive. The necessary gas-warning devices cannot therefore be used directly in these critical environments. The effort needed for safe gas removal for gas measurement/gas warning is very high in case of uncritical temperatures as well.

Extracting the gas by means of SIL (safety integrity level)-approved pumps from the measuring environment and passing the gas through a likewise SIL-approved filter stage, in which the gas is released from condensates (e.g., water) and possibly cooled, is known. The cleaned and cooled gas may then be fed to a gas-warning device. However, the high installation and maintenance efforts needed are drawbacks. Further, the result of the gas measurement is obtained with a time delay, which is due to the filtering, the distance traveled by the gas in the filter section and the cooling off of the gas.

Guiding visible light by means of optical fibers by collimation lenses through a reaction chamber is known from CN 102 062 726 A. This light is fed to a measuring device with an additional optical fiber. The optical fibers are attached to a bracket, which is arranged within the reaction chamber. Such an arrangement is not suitable for large volumes of gas, because the optical measured section through the reactor would be so long that the entire light fed in would be absorbed. Further, the installation and maintenance effort needed in this form of measurement is also very high since the bracket for the optical fibers is arranged within the reaction chamber. For installation, the bracket has to be inserted with effort and has to be removed with high effort for maintenance, which also comprises a cleaning of deposits of reactive gases.

SUMMARY OF THE INVENTION

Hence, an object of the present invention is to provide an in-situ gas-measuring system of the type mentioned in the introduction, in which the installation and maintenance effort needed is reduced and the output of the measured values takes place without undue delay.

According to the invention, an in-situ gas-measuring system is provided comprising an IR photon source and an IR photo detector. The in-situ gas-measuring system has an expansion chamber, at which an optical element is arranged, and a connection element for the detachable, fluid-communicating connection of the expansion chamber to a gas reaction chamber. The IR photon source, the optical element and the IR photon detector define an optical measuring path, which extends through the expansion chamber.

Some terms will be explained in detail below.

An optical measuring path is defined as the path of infrared radiation from the IR photon source through the gas and the optical element to the IR photon detector. The infrared radiation is detected in the IR photon detector.

An optical element is defined as an imaging and/or focusing optical device. The optical element may be configured, for example, as a lens, a mirror or a prism.

For the detachable connection of the expansion chamber to a gas reaction chamber, the expansion chamber may be detachably connected to a gas reaction chamber by means of the connection element. Because the expansion chamber is detachably connected to the gas reaction chamber by means of the connection element, the expansion chamber can be separated from the gas reaction chamber. In this way, the interior space of the gas reaction chamber can be cleaned in order to eliminate impurities, which may form in the optical measuring path due to the hot, cold or reactive gases. As a result, the installation and maintenance effort needed for the gas-measuring device is low. Further, the expansion chamber can be replaced in a fast and flexible manner, so that either a replacement of the expansion chamber or a fast repair can be carried out, for example, in case of damages, without great effort. The gas in the gas reaction chamber may flow into the expansion chamber due to the connection and consequently reach the optical measuring path, which extends from the IR photon source to the expansion chamber, via the optical element and to the IR photon detector. The gas, which is located in the optical measuring path, can then be measured by means of optical methods. The gas may then thus be measured in-situ, unfiltered and without pumping out, so that a time delay of the measured data in case of gas concentrations changing over time is avoided.

The IR photon source is advantageously connected to the expansion chamber via a waveguide, the waveguide comprising a section of the optical measuring path. Further, the IR photon detector may advantageously be connected to the expansion chamber via a waveguide, the waveguide comprising a section of the optical measuring path. The IR photon source and the IR photon detector can thus be arranged at a distance from the expansion chamber and the entire gas reaction chamber. The IR photon source and the IR photon detector are thus protected against vibrations and high or cold temperatures that may originate from the gas reaction chamber.

The waveguides are advantageously sapphire waveguides. Sapphire waveguides withstand very high temperatures and may in this way be arranged at very hot gas reaction chambers without being damaged.

The optical element is advantageously arranged in an interior space of the expansion chamber. The optical element may be installed and adjusted in the interior space without great effort. Thus, the maintenance is also simplified when the optical element has to be cleaned.

As an alternative or in addition, it is advantageous when the optical element is arranged in the wall or at the wall of the expansion chamber. Thus, the optical element is partially shielded from the gases to be measured. The installation and maintenance effort is thus further reduced.

An optical element is advantageously arranged at an end of a waveguide at the expansion chamber. In this case, preferably two optical elements that are arranged at the expansion chamber may be provided. The optical element may in this way form the end of the waveguide and as a result be integrated into the waveguide. The effort needed for installation is further reduced in this embodiment.

The optical element may advantageously be configured as a convergent lens, as a concave mirror or as a collimator lens. The focus is thereby selected such that the infrared radiation is guided into the IR photon detector.

The in-situ gas-measuring system advantageously has a closing element that is configured to block the fluid-communicating connection between the gas reaction chamber and the expansion chamber. In this connection, the closing element may be integrated into the connection element. Further, the connection element may be detachably connected to the expansion chamber. With the closing element closed, the expansion chamber may be detached from the gas reaction chamber by means of the closing element, without the entire gas in the gas reaction chamber having to be removed. In this way, a fast replacement of the expansion chamber may be carried out.

The expansion chamber advantageously has an expansion chamber closing element. The expansion chamber may as a result be closed separately. The expansion chamber may be detached from the gas reaction chamber especially combined with a closing element at the connection element at any time and maintenance can be performed. Further, the gas which was measured may remain in the expansion chamber, so that it may be available for additional measurements far away from the gas reaction chamber.

The present invention will be explained in detail on the basis of an advantageous embodiment by means of the attached drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
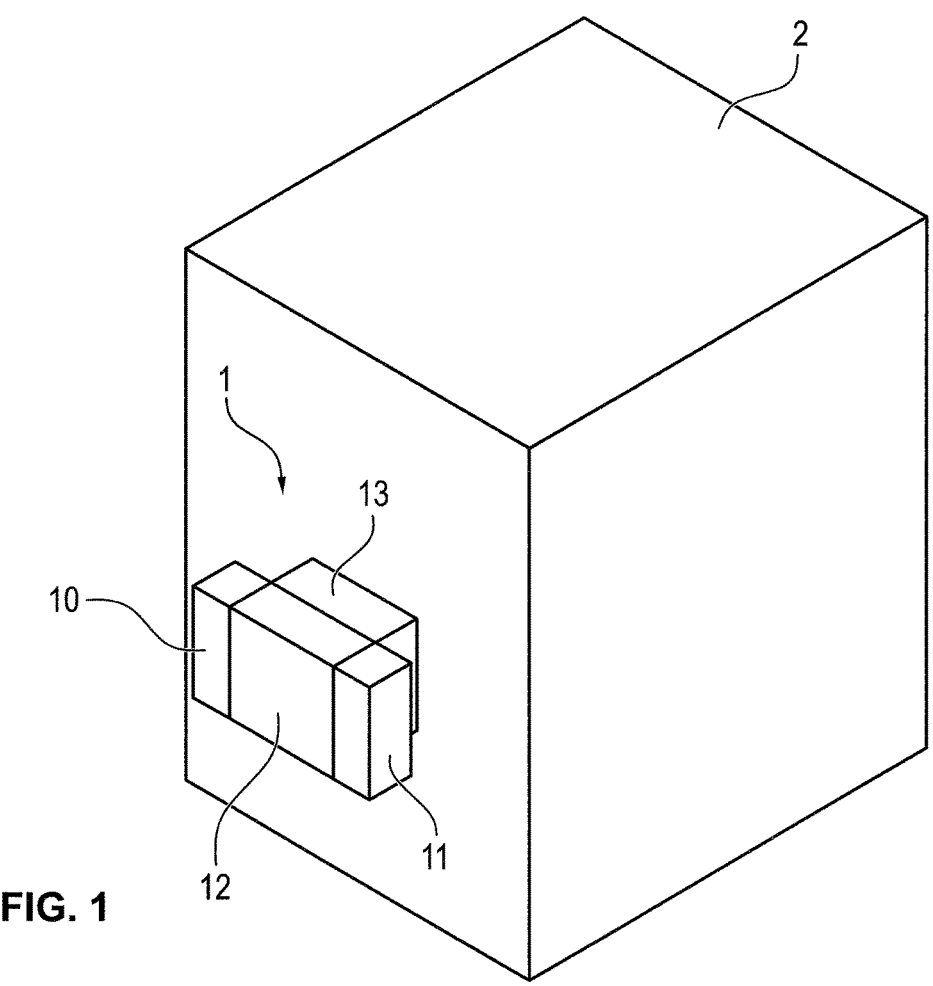
FIG. 1 is a schematic view of the in-situ gas-measuring system at a gas reaction chamber.

Referring to the drawings the in-situ gas-measuring system is referenced in its entirety with the reference number 1.

FIG. 1 shows an in-situ gas-measuring system 1, which is arranged at a gas reaction chamber 2. The in-situ gas-measuring system 1 comprises an expansion chamber 12, which is detachably connected to the gas reaction chamber 2 by means of a connection element 13. Further, the in-situ gas-measuring system 1 comprises an IR photon source 10 and an IR photon detector 11. The IR photon source 10 emits infrared radiation into the expansion chamber 12. The IR photon detector 11 collects the emitted infrared radiation, which is passed through the expansion chamber 12 and to the gas located in the expansion chamber 12. The infrared radiation is thus transmitted by the IR photon source 10 through the expansion chamber 12 to the IR photon detector 11. In this case, the expansion chamber 12 has the same gas atmosphere as the gas reaction chamber 2. The gas composition or gas concentration in the gas reaction chamber 2 can thus be determined directly by means of the measurement.

The measurement of the gases thereby takes place in-situ, so that a delay-free measurement is made possible. In this case, an optical element 16, which focuses the infrared radiation emitted by the IR photon source 10 to the IR photon detector 11, is provided at the expansion chamber 12. The IR photon source 10, the optical element 16 and the IR photon detector 11 define an optical measuring path through the expansion chamber 12.

Figure 2:
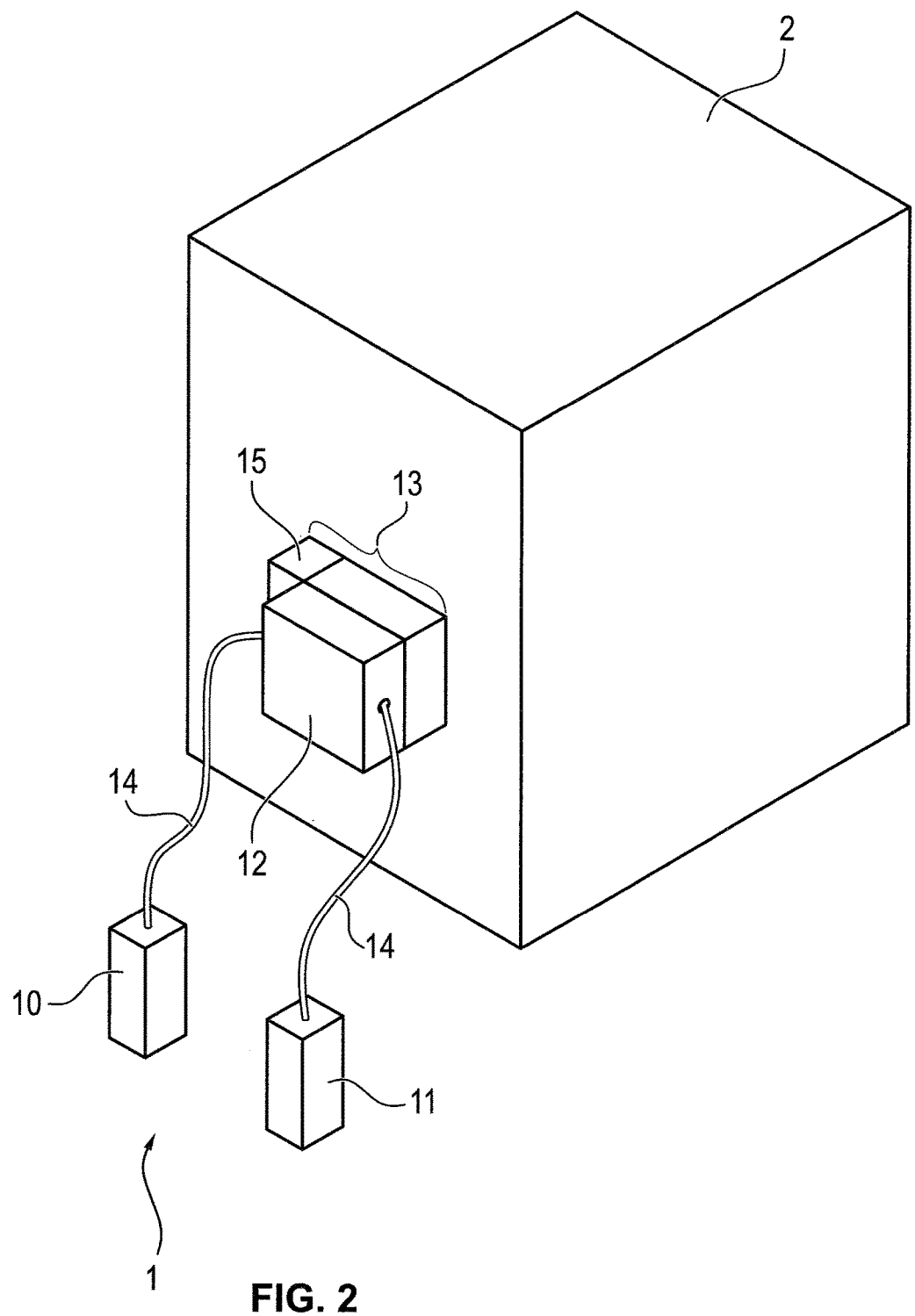
FIG. 2 is a schematic view of an in-situ gas-measuring system with waveguides.

According to FIG. 2, the IR photon source and the IR photon detector 11 may be connected to the expansion chamber 12 via waveguides 14. In this connection, the IR photon source 10 transmits the infrared radiation through one of the waveguides 14 into the expansion chamber 12. An additional waveguide 14 transmits the infrared radiation being released from the expansion chamber 12 to the IR photon detector 11. The IR photon source 10 and the IR photon detector 11 may in this case be arranged spaced apart from the expansion chamber 12 and thus also from the gas reaction chamber 2. Vibrations and temperature fluctuations and high or low temperatures, which originate from the gas reaction chamber 2, thus cannot influence the measurement and the emission of the photons. The IR photon source 10 and the IR photon detector 11 may be arranged at a safe distance from the gas reaction chamber 2 by means of the waveguides 14.

In this case, the waveguides 14 are made of sapphire. Due to the material of the waveguides 14, the waveguides 14 may also be used in gas reaction chambers that emit high temperatures. Further, sapphire has the advantage that sapphire is transmissive for infrared radiation.

The expansion chamber 12 is further detachably connected to the connection element 13. In this case , the connection element 13 comprises a closing element 15, which can block the fluid-communicating connection between the expansion chamber 12 and the gas reaction chamber 2. In this way, the fluid-communicating connection between the expansion chamber 12 and the gas reaction chamber 2 can be cut, so that no more gas reaches the expansion chamber 12 from the gas reaction chamber. The expansion chamber 12 may be separated from the connection element 13 with the closing element 15 closed, so that the interior space 120 of the expansion chamber 12 can be cleaned. Further, an expansion chamber 12 can be replaced in this way.

Figure 3A:
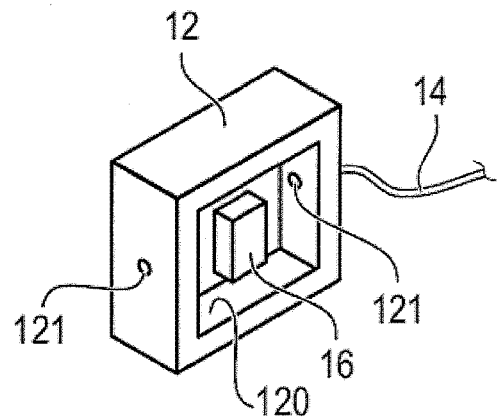
FIG. 3a is a schematic view of the interior space of an expansion chamber of a first alternative embodiment.
Figure 3B:
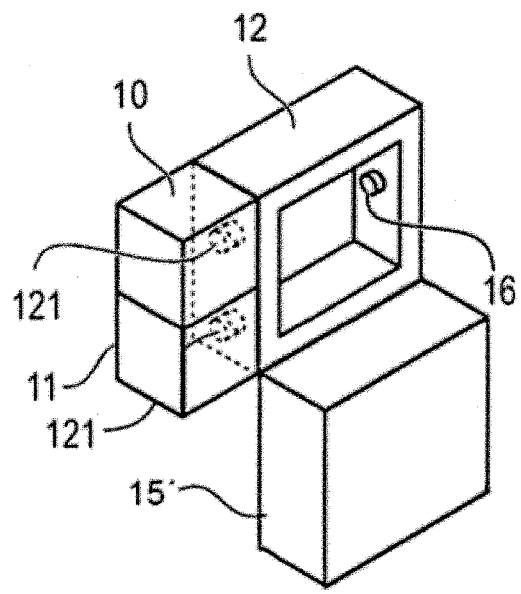
FIG. 3b is a schematic view of the interior space of an expansion chamber of another alternative embodiment.
Figure 3C:
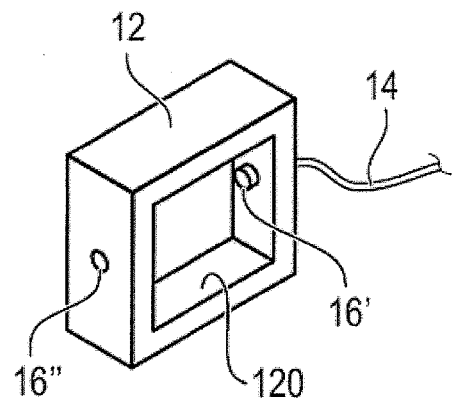
FIG. 3c is a schematic view of the interior space of an expansion chamber of another alternative embodiment.

FIGS. 3a, 3b and 3c show an interior space 120 of an expansion chamber 12. In a first alternative embodiment according to FIG. 3a an optical element 16 is arranged within the expansion chamber 12 in the interior space 120. The expansion chamber 12 additionally comprises openings 121. The openings 121 are used to introduce the infrared radiation of the IR photon source 10 into the expansion chamber 12 and to enable the IR photon detector 11 to detect the infrared radiation in the expansion chamber 12. The openings 121 are thus used to guide the infrared radiation through the expansion chamber 12 or through the interior space 120 of the expansion chamber 12.

With the alternative embodiment of FIG. 3a, the optical element 16 is arranged such that it focuses the infrared radiation that is emitted by the IR photon source 10 into the opening 121, which is associated with the IR photon detector 11. The openings 121 may in this case be connected via waveguides 14 to the IR photon detector 11 or the IR photon source 10. As an alternative, the IR photon source 10 and the IR photon detector 11 may be arranged directly behind the openings 121. The IR photon detector 11 and the IR photon source 10 are arranged directly at the expansion chamber 12 in the alternative according to FIG. 3a. Further, the openings 121 are arranged in the wall of the expansion chamber 12 on opposite sides. The measuring path is consequently defined as beginning at the IR photon source 10 through the one opening 121, the expansion chamber 12 and the optical element 16 to the second opening 121 and as ending at the IR photon detector 11. In this case, the optical element 16 may be a convergent lens.

In an alternative embodiment according to FIG. 3b, the optical element 16 may be configured as a concave mirror or as another reflective element. In this embodiment, the openings 121 are arranged such that infrared radiation which is guided from the one opening 121 to the optical element 16 is guided from the optical element 16 into the other opening 121. In this case, the optical element 16 is configured as a concave mirror. The IR photon source 10 and the IR photon detector 11 may be arranged directly at the expansion chamber behind the openings 121 in this embodiment as well. As an alternative, the IR photon source 10 and the IR photon detector 11 may be connected to the openings 121 via waveguides 14.

In this embodiment, the expansion chamber 12 comprises an expansion chamber closing element 15'. The detachment of the expansion chamber 12 from the gas reaction chamber 2 is thus simplified. Further, gas, which can be further measured at a later time at another site, may remain in the expansion chamber 12.

In another alternative embodiment according to FIG. 3c, a first optical element 16' and a second optical element 16" are provided. In this case, the optical elements 16', 16" are arranged in the wall of the expansion chamber 12. They may be configured as collimator lenses. Infrared radiation, which is introduced from outside through the optical elements 16', 16" into the expansion chamber 12, passes through the interior space 120 of the expansion chamber 12 as collimated infrared radiation, i.e., with parallel beams. This has the advantage that the circulation of gas in the interior space 120 of the expansion chamber 12 is not changed by an optical element 16, which is placed in the interior space 120 of the expansion chamber 12. Hence, the gas composition in the expansion chamber 12 corresponds to the gas composition in the gas reaction chamber 2. Changes, which may occur due to disturbed flow conditions, are thus avoided.

The present invention thus avoids the installation of multistage pumping and filtering units, which transport filtered and cooled gas to the gas-warning devices.

While specific embodiments of the invention have been shown and described in detail to illustrate the application of the principles of the invention, it will be understood that the invention may be embodied otherwise without departing from such principles.

What is claimed is:

1. A gas-measuring system comprising:
   an IR photon source;
   an IR photon detector;
   an expansion chamber having an interior gas space;
   an optical element arrangement operatively connected with the expansion chamber and defining an optical measuring path which extends through the expansion chamber;
   a photon source waveguide connected to the optical element arrangement and operatively connecting the IR photon source to the interior gas space of the expansion chamber, wherein the photon source waveguide comprises a section of the optical measuring path and the IR photon detector is positioned outside of the interior gas space of the expansion chamber and arranged at a distance from the expansion chamber away from the expansion chamber;
   a photon detector waveguide connected to the optical element arrangement and operatively connecting the IR photon detector to the interior gas space of the expansion chamber wherein the photon detector waveguide comprises a section of the optical measuring path and the IR photon detector is positioned outside of the interior gas space of the expansion chamber and arranged at a distance from the expansion chamber from the expansion chamber; and
   a connection element detachably and fluid-communicatingly connecting the expansion chamber to a gas reaction chamber, whereby gas in the reaction chamber flows into the interior gas space of the expansion chamber and gas pressure in the interior gas space of the expansion chamber is equalized with gas pressure in the gas reaction chamber, wherein the IR photon source, the optical element and the IR photon detector define an optical measuring path, which extends through the expansion chamber.

2. A gas-measuring system in accordance with claim 1, wherein the waveguide is a sapphire waveguide.

3. A gas-measuring system in accordance with claim 1, wherein the optical element arrangement comprises first and second optical elements that are each arranged in the interior space of the expansion chamber.

4. A gas-measuring system in accordance with claim 1, wherein the optical element arrangement comprises first and second optical elements that are each arranged in a wall of the expansion chamber.

5. A gas-measuring system in accordance with claim 1, wherein the optical element arrangement comprises an optical element that is arranged at an end of each waveguide.

6. A gas-measuring system in accordance with claim 1, wherein the optical element arrangement comprises a convergent lens or a concave mirror or a collimator lens or any combination of a convergent lens, a concave mirror and a collimator lens.

7. A gas-measuring system in accordance with claim 1, further comprising a closing element configured to block the fluid-communicating connection between the expansion chamber and a gas reaction chamber.

8. A gas-measuring system in accordance with claim 7, wherein the closing element is integrated into the connection element.

9. A gas-measuring system in accordance with claim 7, wherein the expansion chamber and the connection element are configured separately, wherein the closing element is integrated into the connection element.

10. A gas-measuring system in accordance with claim 1, wherein the expansion chamber has an expansion chamber closing element.

11. A gas-measuring system in accordance with claim 7, wherein the expansion chamber has an expansion chamber closing element containing expansion chamber gas within the expansion chamber such that expansion chamber gas remains in the expansion chamber upon detachably disconnecting the connection element from the gas reaction chamber to isolate the expansion chamber from the gas reaction chamber and from an environment.

12. A gas-measuring system in accordance with claim 1, further comprising a closing element configured to block the fluid-communicating connection between the expansion chamber and a gas reaction chamber and configured to contain expansion chamber gas within the expansion chamber such that expansion chamber gas that had entered from the gas reaction chamber remains in the expansion chamber upon detachably disconnecting the connection element from the gas reaction chamber to isolate the expansion chamber from the gas reaction chamber and from an expansion chamber environment.

13. A gas-measuring system in accordance with claim 1, wherein:
 the optical element arrangement comprises a first optical element arranged in a wall of the expansion chamber and a second optical element arranged in a wall of the expansion chamber;
 the first optical element is arranged at an end of the photon source waveguide and the second optical element is arranged at an end of the photon detector waveguide; and
 the first and second optical elements comprise a convergent lens or a concave mirror or a collimator lens or any combination of a convergent lens, a concave mirror and a collimator lens.

* * * * *